United States Patent [19]
Nelson et al.

[11] Patent Number: 5,800,428
[45] Date of Patent: Sep. 1, 1998

[54] LINEAR CATHETER ABLATION SYSTEM

[75] Inventors: Dale K. Nelson, Minneapolis; Steven D. Savage, Paynesville; Brad D. Pedersen, Minneapolis; Whitney A. McFarlin, Wayzata, all of Minn.

[73] Assignee: Angeion Corporation, Plymouth, Minn.

[21] Appl. No.: 651,530

[22] Filed: May 16, 1996

[51] Int. Cl.⁶ .................................... A61B 17/39
[52] U.S. Cl. ................ 606/41; 606/45; 607/105
[58] Field of Search ................ 606/41, 42, 45–50; 607/100–102, 104, 105

[56] References Cited

U.S. PATENT DOCUMENTS

| | | | |
|---|---|---|---|
| 4,269,174 | 5/1981 | Adair | 606/50 |
| 4,524,770 | 6/1985 | Orandi | 606/46 |
| 4,869,248 | 9/1989 | Narula. | |
| 5,007,908 | 4/1991 | Rydell | 606/50 |
| 5,078,717 | 1/1992 | Parins. | |
| 5,083,565 | 1/1992 | Parins. | |
| 5,125,928 | 6/1992 | Parins. | |
| 5,222,938 | 6/1993 | Parins. | |
| 5,263,493 | 11/1993 | Avitall. | |
| 5,281,218 | 1/1994 | Imran. | |
| 5,324,284 | 6/1994 | Imran. | |
| 5,327,889 | 7/1994 | Imran. | |
| 5,334,193 | 8/1994 | Mardella. | |
| 5,336,222 | 8/1994 | Durgin, Jr. et al. | 606/50 |
| 5,342,357 | 8/1994 | Nardella | 606/50 |
| 5,348,554 | 9/1994 | Imran. | |
| 5,403,311 | 4/1995 | Abele et al. | 606/49 |
| 5,423,811 | 6/1995 | Imran. | |
| 5,431,649 | 7/1995 | Mulier. | |
| 5,454,370 | 10/1995 | Avitall. | |
| 5,458,597 | 10/1995 | Edwards et al. | 606/41 |
| 5,462,521 | 10/1995 | Brucker. | |
| 5,476,495 | 12/1995 | Kordis. | |
| 5,487,385 | 1/1996 | Avitall. | |
| 5,514,130 | 5/1996 | Baker | 606/41 |

*Primary Examiner*—Michael Peffley
*Attorney, Agent, or Firm*—Brad D. Pedersen

[57] ABSTRACT

A radio frequency (RF) ablation catheter system utilizes a flexible, tubular electrode that is selectively extendable from a distal end of a catheter body. The flexible, tubular electrode creates a continuous linear lesion when a longitudinal side of the electrode is arcuately positioned against an interior wall of the human body and the electrode is energized while a cooling fluid passes through the electrode. The catheter system also includes mechanisms for remotely manipulating and extending the electrode. Preferably, the catheter body include a catheter shaft and a flexible tip section such that the distal end of the catheter is steerable. The invention also includes a method of operating the RF catheter ablation system so as to create arcuate linear lesions.

33 Claims, 7 Drawing Sheets

LINEAR CATHETER ABLATION SYSTEM

FIELD OF THE INVENTION

The present invention relates generally to the field of mapping and ablation using steerable vascular catheters. More particularly, the present invention is directed to a radio frequency (RF) catheter ablation system that can create continuous linear lesions.

BACKGROUND ART

Steerable catheter ablation systems are well know for the identification and treatment of a variety of medical conditions. Catheters of this type have one or more electrodes on the far or distal end of a catheter which is inserted into a blood vessel or similar bodily area and steered toward a body part. Once in position, the electrodes can be used for electrically mapping the body part, or for delivering a therapy to the body part.

Catheter ablation was originally developed to treat various vascular diseases by removing blockages in the arteries, for example, as shown by the catheter ablation systems described in U.S. Pat. Nos. 5,078,717 and 5,125,928. Catheter ablation has also been used for thermal ablation treatments of other body organs, as taught, for example, in U.S. Pat. No. 5,222,938. One area where the use of steerable catheter ablation systems has meet with substantial success is in the field of cardiac electrophysiology, particularly for treatment of abnormal heart rhythms known as cardiac arrhythmias. In treating cardiac arrhythmias, the goal of the catheter ablation procedure is to identify the tissue in the heart that may be causing the arrhythmia, and then selectively destroy or disable that tissue without damaging surrounding tissue and muscle.

Identification of a potential ablation site is often done by a process known as mapping in which a catheter having multiple electrodes is inserted into the heart and the electrical signals of the heart are monitored in order to identify the tissue causing the arrhythmia. Examples of these types of catheter mapping systems are shown in U.S. Pat. Nos. 5,263,493, 5,324,284, 5,327,889, 5,454,370, 5,476,495 and 5,487,385. In each of these systems, a plurality of separate electrodes are mounted on one or more flexible members that are then positioned against the interior of a chamber of the heart. In this way, the discrete electrodes each serve as individual antennas for detecting the electrical activity of the heart in the area corresponding to that electrode.

Once an ablation site is identified, a lesion is created that permanently destroys the ability of the cells to propagate the electrical signals of the heart. Early cardiac catheter ablation systems, such as shown in U.S. Pat. No. 4,869,248, utilized a DC current directed through a thin loop of wire at the end of the catheter to burn a lesion around the arrhythmia-producing tissue. Unfortunately, the use of a DC current to heat the wire generated excess heat which caused undesirable coagulation of the blood at the site of the ablation. Another problem was that the wire loop was relatively imprecise, especially for treating small amounts of tissue.

To overcome these problems, most current cardiac catheter ablation systems use a more controlled type of energy source, such as radio frequency (RF) energy, to heat the tissue above 55° C., thereby creating the desired lesion. The more controlled RF energy is also delivered in a more precise manner by using a point source of ablation energy. Examples RF catheter ablation systems which deliver the RF energy as a point source using a needle-like or tip electrode fixed to the distal end of the catheter are shown in U.S. Pat. Nos. 5,083,565, 5,281,218 and 5,403,311. Another solution to the problem of excess heat generation has been to use a coolant to control the temperature of the ablation electrode. Examples of fluid cooled RF ablation catheter systems are shown in U.S. Pat. Nos. 5,334,193, 5,348,554, 5,423,811, 5,431,649 and 5,462,521.

While existing RF catheter ablation systems are well-suited for use in the ablation of localized arrhythmia producing tissue that can be destroyed by using a point source of ablation energy, recent techniques have been developed which require that the ablation energy be delivered as something other than a point source. Once such procedure is the Maze and Corridor procedure developed by Dr. Cox et al. of Washington School of Medicine in St. Louis, Mo. As originally developed, this procedure treats atrial fibrillation or flutter by slicing the atrial tissue in a maze-like pattern in order to prevent the conduction of fibrillation electrical activity through the atrium. It has been discovered that this procedure can also be accomplished by ablation, however, the time and effort required to ablate the extensive maze-like pattern required by this procedure using only a point source of ablation energy makes it generally impractical to attempt this procedure with existing tip electrode RF ablation catheter systems because of the difficulty in dragging a tip electrode across tissue to create a linear lesion.

U.S. Pat. No. 5,487,385 describes an RF atrial mapping and ablation catheter system which is particularly adapted to create the linear lesions necessary to perform procedures such as the Maze and Corridor procedure. In this patent, a flexible working catheter section is provided with a plurality of spaced-apart ring electrodes that are used for both sensing and ablation. The working catheter section is extendable from a main catheter sheath and may be controlled to generate an adjustable arcuate curve that can be positioned against an interior wall of the heart to perform both sensing and ablation. While the use of the same set of electrodes for both mapping and ablation has the advantage of requiring only a single catheter to perform both steps of the procedure, it has a disadvantage in that the nature of the electrodes must be a compromise between a pure sensing electrode and a pure ablation electrode. This comprise, in turn, can affect the quality and consistency of the linear lesions which are created using this system. The use of multiple spaced-apart electrodes also makes it necessary to increase the power utilized by the system in order to ensure that the lesions which are created by each individual electrode will be large enough to overlap so as to create the desired linear lesion. This not only causes potential problems with respect to destroying more heart tissue than may be necessary to accomplish the procedure, but also increases the possibility of undesired coagulation of blood at the site due to the higher temperatures created by the increased energy usage. In addition, the existence of multiple electrodes increases the possibility of both mechanical and electrical failure within the system.

Although RF catheter ablation systems have wide application in a variety of medical procedures, most RF catheter ablation systems are not suited for use in creating linear lesions. Accordingly, it would be desirable to provide for an RF catheter ablation system which is simple and reliable, yet is capable of generating high quality, consistent linear lesions.

SUMMARY OF THE INVENTION

The present invention is a radio frequency (RF) ablation catheter system that utilizes a flexible, tubular electrode that is selectively extendable from a distal end of a catheter body. The flexible, tubular electrode creates a continuous linear lesion when a longitudinal side of the electrode is arcuately positioned against an interior wall of the human body and the electrode is energized while a cooling fluid passes through the electrode. The catheter system also includes mechanisms for remotely manipulating and extending the electrode. Preferably, the catheter body include a catheter shaft and a flexible tip section such that the distal end of the catheter is steerable. The invention also includes a method of operating the RF catheter ablation system so as to create arcuate linear lesions.

The present invention provides a simple and reliable RF catheter ablation system for generating high quality, consistent linear lesions. The use of a cooling fluid allows for more accurate control of the temperature of the electrode, thereby creating high quality, consistent linear lesions. The flexible, tubular electrode is preferably a small, flexible syringe-like needle made of Nintonal® or other highly flexible, high quality stainless steel or alloy tubing having an outer diameter ranging from 0.1 mm–0.5 mm and having a tensile strength ranging from 50,000–500,000 psi with a high modulus of elasticity. The spring-like flexibility of the tubular electrode allows arcuate curves to be created having a chord depth of up to 20 mm for electrode lengths of up to 5 cm.

In various embodiments of the present invention, the distal end of the electrode may be provided with a radiopaque plastic sphere to aid in positioning the electrode under flouroscopy and to prevent the end of the electrode from penetrating tissue. The electrode may be provided with micro-perforations or micro-slots so as to allow for dispersion of the cooling fluid at locations other than the distal end of the electrode. The electrode may be constructed of a heat shape memory metal that is pre-formed to a desired shape prior to the procedure and that will assume that desired shape upon heating the electrode to a given activation temperature and will return to a straight shape after the procedure is completed and the temperature of the electrode is allowed to drop. Preferably, the electrode may be provided with a mapping electrode located on the distal end of the catheter body to allow for sensing and measurement of the electrical activity of the heart, and a heat sensor, such as a thermocouple or thermistor, to allow the physician to monitor the electrode temperature during the procedure. The distal end of the catheter body can include structure to establish a seal between the catheter and the electrode that is impervious to body fluids. During extension and positioning of the electrode, a guide member may be present within the interior channel of the electrode to provide additional structural integrity to the electrode, with the guide member being withdrawn prior to flushing coolant through the electrode. Preferably, coolant is passed through the electrode at a flow rate that does not exceed 2 ml/minute.

In an alternate embodiment, the tubular electrode may be comprised of multiple, flexible tubular electrodes so as to form a wide-variety of possible lesion patterns in a single use of the ablation system. In one embodiment, three or more flexible, tubular electrodes are positioned in a spaced-apart, side-by-side planar arrangement so as to create a "crow's foot" ablation pattern. In another embodiment, three or more flexible, tubular electrodes are positioned in spaced-apart, side-by-side spherical arrangement so as to create a three-dimensional basket-like ablation pattern.

DESCRIPTION OF THE PREFERRED EMBODIMENT(S)

The present invention is a radio frequency (RF) linear catheter ablation system that is designed to create a precise, continuous linear lesion when a longitudinal side of an electrode is positioned against an interior wall of a human body and the electrode is energized. The present invention is particularly suited for cardiac ablation procedures, such as the Maze and Corridor ablation procedure, where it is necessary to generate one of more linear lesions within the heart as part of the therapeutic procedure. The present invention may also have application in catheter ablation procedures related to other body parts where there is a need to create high quality, finely controlled linear lesions, such as an at least a partial circular lesion created around a valve orifice.

Figure 1:
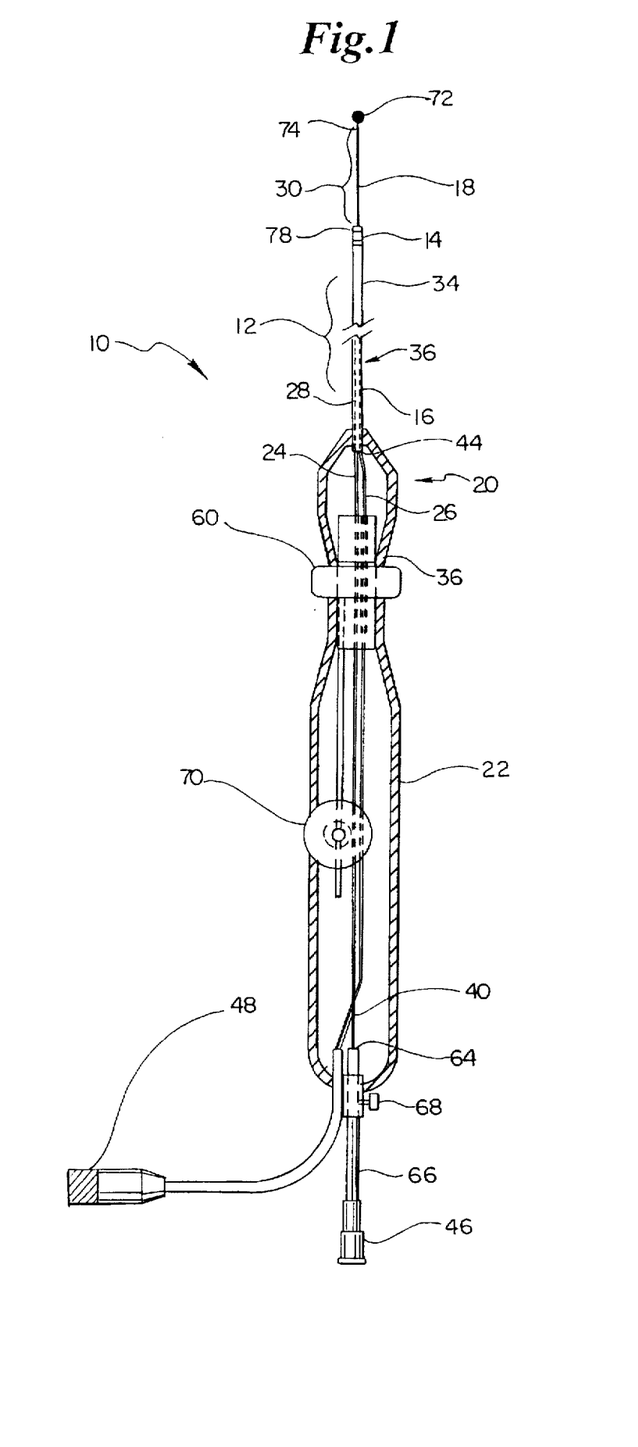
FIG. 1 is a schematic representation of an RF catheter ablation system in accordance with the present invention with the flexible electrode shown in an extended, straight position.

Referring now to FIG. 1, the preferred embodiment of an RF linear catheter ablation system in accordance with the present invention will be described. An RF linear catheter ablation system 10 broadly includes a flexible, elongated catheter body 12 having a distal end 14 and a proximal end 16, a flexible, tubular electrode 18 and mechanisms 20 for operating the catheter system, including a handle 22 for remotely manipulating and selectively extending electrode 18 from distal end 14, structure 24 for providing a cooling fluid which passes through electrode 18, and structure 26 for providing an RF energy to electrode 18. Catheter body 22 is comprised of a flexible, nonconductive, biocompatible material having at least one lumen 28 therethrough. Catheter body 12 may be of varying lengths, the length being determined by the particular needs of a given catheter ablation procedure. Preferably, catheter body 28 has an outer diameter ranging from 4–12 French and is constructed of a thermoplastic, such as nylon, in which a braiding is embedded. Lumen 28 is of sufficient diameter to accommodate mechanisms 20. In a preferred embodiment, catheter body has an outer diameter of 8 French and lumen 28 ha a diameter of 3 French.

Figure 13:
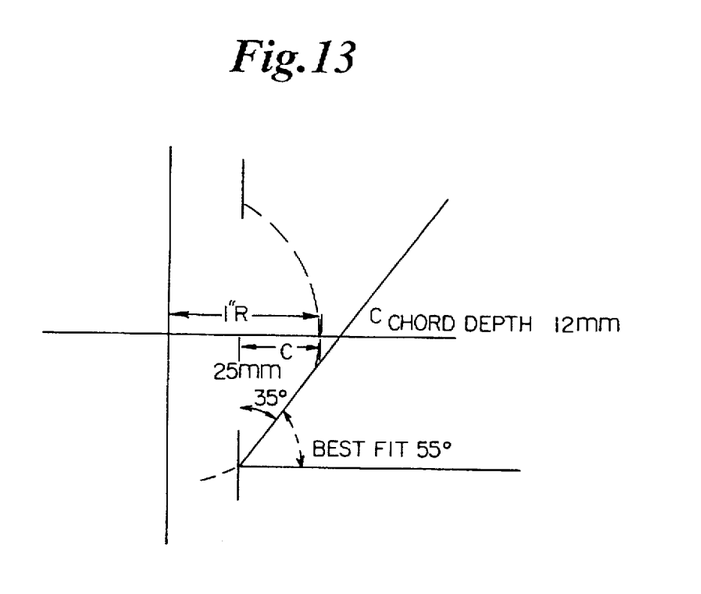
FIG. 13 is a schematic representation of the range of arcuate curves achievable by the present invention.

Flexible, tubular electrode 18 is preferably a small, flexible syringe-like needle made of Nintonal® or other similar high quality stainless steel or alloy tubing having an outer diameter ranging from 0.05 mm–0.5 mm and having a tensile strength ranging from 50,000–500,000 psi. Preferably, tubular electrode 18 has a modulus of elasticity which ranges from that of standard stainless steel to that of Nintonal® or similar heat memory shape metals. As discussed with reference to FIG. 13, the spring-like flexibility of tubular electrode allows arcuate curves to be created having a chord depth of up to 20 mm for electrode lengths of up to 5 cm. In a preferred embodiment, tubular electrode 18 has a generally circular cross-sectional area, however, it will be recognized that tubular electrode 18 can be constructed with any cross-sectional area shape. The length of electrode 18 may range from 0.5 cm–10 cm, depending upon the desired length of the linear lesion to be created and upon the degree of flexibility and force which can be exerted by distal end 14 of catheter body 12 to urge a longitudinal side 30 of electrode 18 against or into an interior wall of the human body as shown in FIGS. 9–12.

In the preferred embodiment as shown in FIG. 1, catheter body 12 includes a main catheter shaft 32 and a steerable distal tip section 34, and mechanisms 20 for operating the catheter system further comprises structure 36 for remotely manipulating steerable distal tip section 34. Preferably steerable distal tip section 34 is relatively short portion of the length of catheter body 12, typically having dimensions in the range of 1 cm to 15 cm. In the embodiment, distal tip section 34 is manipulated, for example, either by deflection induced by structure 36, or by rotation of catheter body 12 or handle 22, or by any combination thereof. It will be understood that any number of the various techniques known in the art of catheters for manipulating or steering a distal tip section of the catheter may be employed with the present invention.

Figure 5:
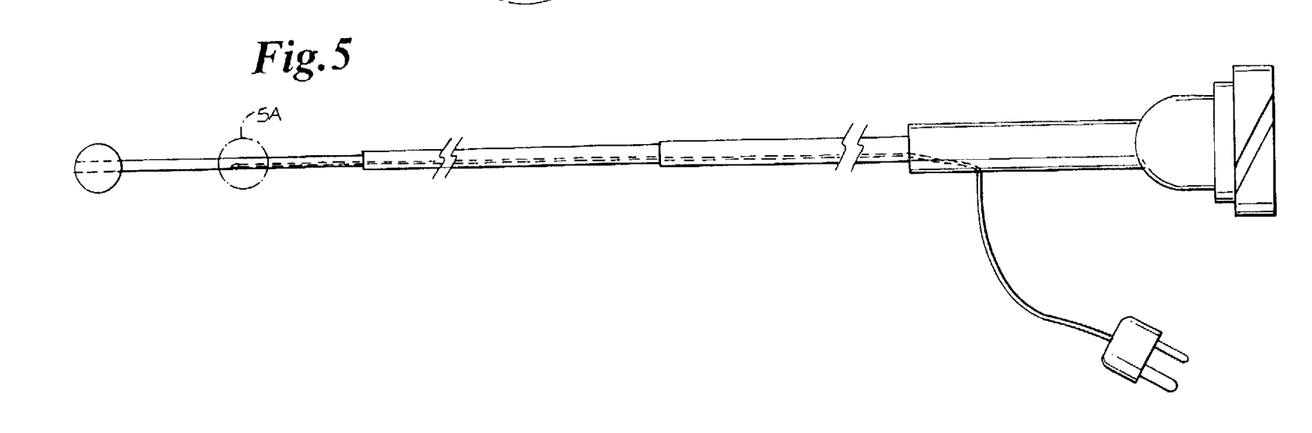
FIG. 5 is detailed schematic representation of a preferred embodiment of the electrode portion of the present invention showing a heat sensor.

As shown in FIGS. 1 and 5, in this embodiment structure 24 for providing the cooling fluid and structure 26 for providing the RF energy comprise a flexible, conductive hollow shaft 40 disposed with lumen 28 of catheter body 12. Shaft 40 has a distal end 42 operably connected to electrode 18 and a proximal end 44 operably connected to a cooling fluid source (not shown) by fluid interface port 46 and to an RF energy source (not shown) by an electrical interface port 48. In a preferred embodiment, fluid interface port 44 is a standard Luer fitting and electrical interface port 48 is a quick disconnect connector or a standard multi-pin connector.

Figure 7:
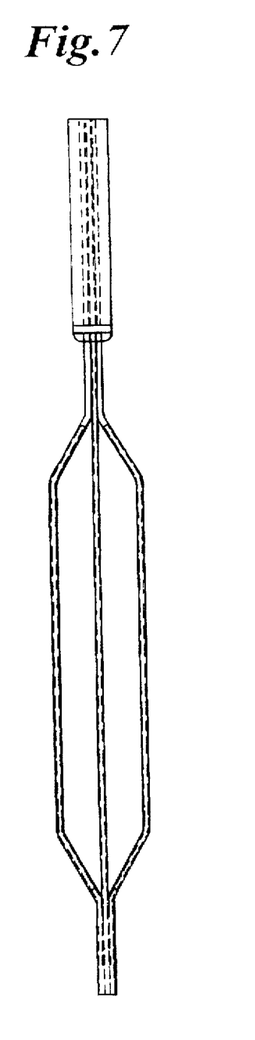
FIG. 7 is a schematic representation of an alternate embodiment of the present invention having multiple flexible electrodes configured in a planar arrangement.
Figure 8:
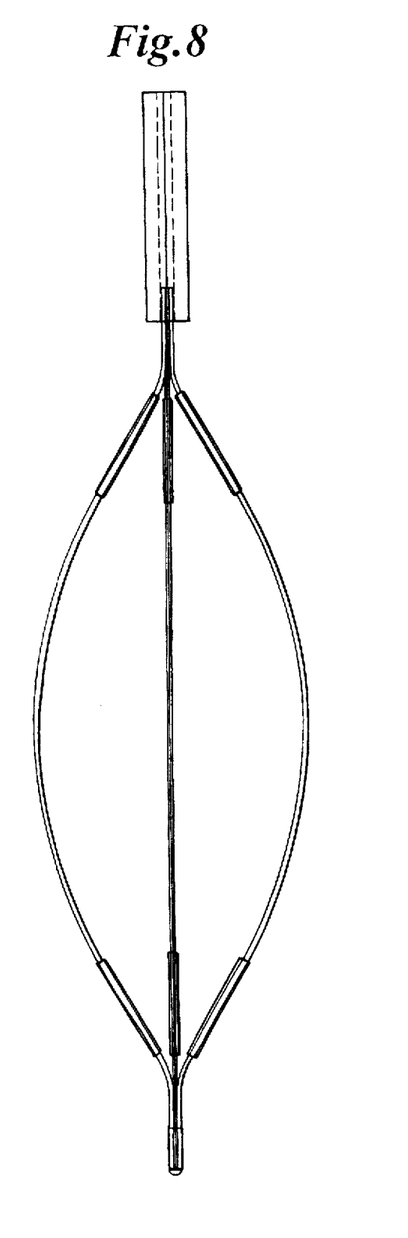
FIG. 8 is a schematic representation of an alternate embodiment of the present invention having multiple flexible electrodes configured in a spherical arrangement.
Figure 9:
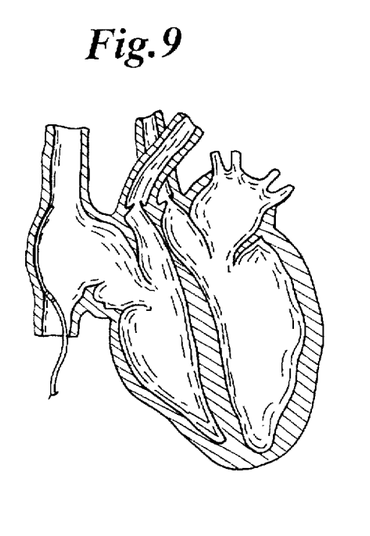
FIGS. 9–12 are cross sectional representations of a human heart showing various embodiments of the present invention positioned within the heart.
Figure 10:
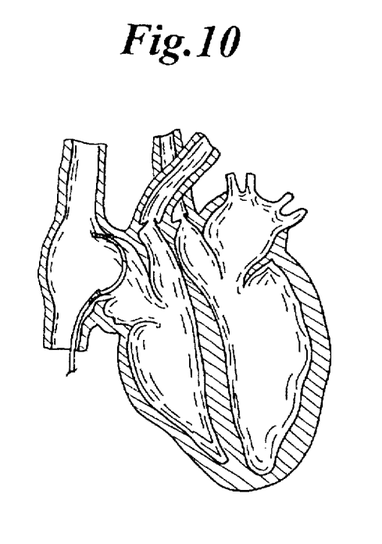
Figure 11:
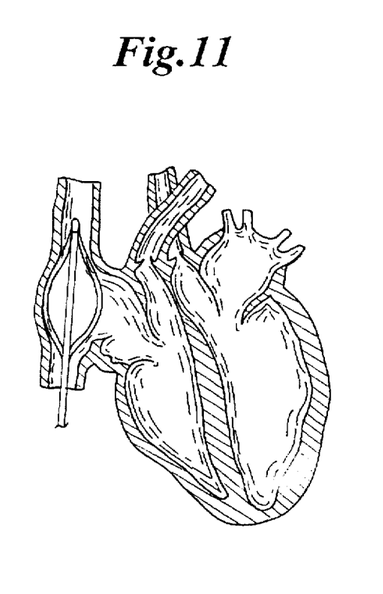
Figure 12:
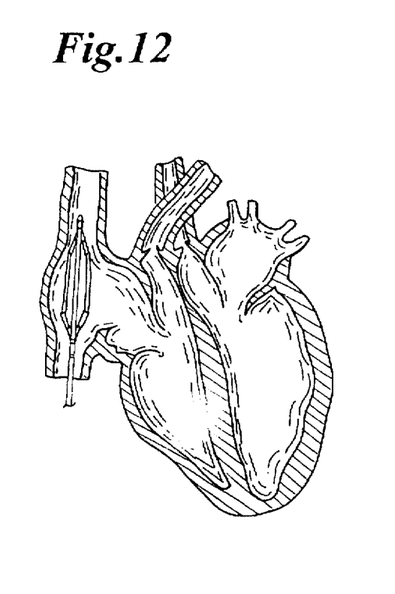

In the multiple electrode embodiment of the present invention as shown in FIGS. 7 and 8, it is contemplated that the connections between electrodes 18 and fluid interface 46 via structure 24 will be made such that the arrangement of the connection is selected from the set consisting of: independent connection of each electrode 18-1, 18-2, or 18-3 to structure 24/interface 46, or common connection of all electrodes 18-1, 18-2, and 18-3 to the structure 24/interface 46. Similarly, the connections between electrodes and electrical interface 48 via structure 26 will be made such that the arrangement of the connections is selected form the set consisting of: independent connection of each electrode 18-1, 18-2, or 18-3 to structure 26/interface 48, or common connection of all electrodes 18-1, 18-2, and 18-3 to the structure 26/interface 48. It will be apparent that handle 22 can be provided with any number of interfaces/ports 46, 48 depending upon the number of connections, both electrical and fluid, that are necessary for a given embodiment of the present invention.

Referring to FIG. 5, hollow shaft 40 and electrode 18 are preferably formed as an integral piece of conductive tubing.

Figure 6:
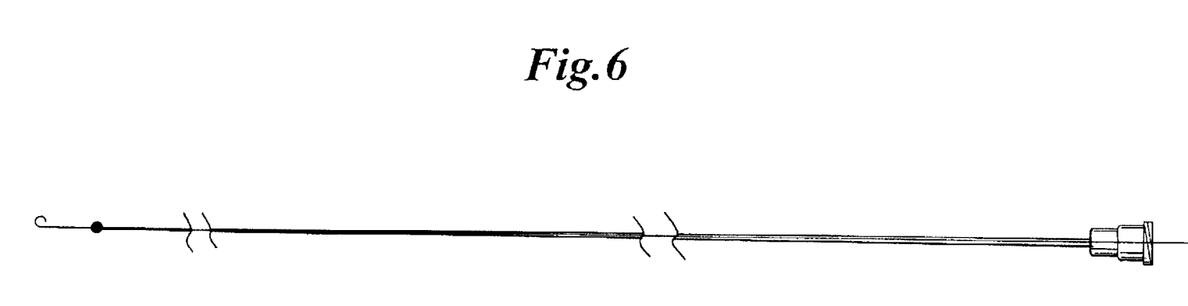
FIG. 6 is a detailed schematic representation of an alternate embodiment of the electrode portion of the present invention showing a guide member.

In the embodiment shown in FIG. 5, this integral piece of conductive tubing is comprised of a series of three tubes 50, 52 and 54 of varying diameters which are fixed connected together in a coaxial, end-to-end manner. Electrode 18 comprises the most distal tube 50 and preferably has dimensions of 0.014×0.009×4.5". A second most distal tube 52 has a distal end welded to a proximal end of tube 50 and has dimensions of 0.021×0.016×10". A third proximal tube 54 has a distal end welded to a proximal end of tube 52 and has dimensions of 0.027×0.021×42". In an alternate embodiment as shown in FIG. 6, shaft 40 is formed of a continuous tube 56 that is continuously tapered. Electrode 18 is formed integral with tube 56, but having a constant diameter. It will be apparent that the inner diameters, outer diameters and mechanical characteristics of tubes 50, 52, 54 and 56 can be selected and arranged in a variety of configuration depending upon the desired pressure drop and mechanical characteristics which are desired. It is contemplated that in this embodiment shaft 40 and electrode 18 will be formed of one or more conductive tubes having a configuration selected from the set consisting of: a continuous tube having a constant diameter, a continuous tube having a continually tapered diameter, a continuous tube having at least a portion of which has a tapered diameter, a series of tubes of varying degrees of flexibility which are fixed connected together in a coaxial, end-to-end manner, a series of tubes of varying diameters which are fixed connected together in a coaxial, end-to-end manner, or any combination thereof. It is preferred that tubes 52, 54 and 56 or hollow shaft 40 which are disposed within catheter body 12 will be provided with a lubricious outer surface or will have a lubricating fluid disposed in the annular space there between to facilitate extension and retraction of electrode 18 relative to catheter body 12.

Referring again to FIG. 1, the preferred embodiment of handle 22, including structure 36 for remotely manipulating the distal tip section 36 includes a flex tip actuator 60 operably connected to catheter body 12 proximate proximal end to control deflection of distal end 14 of catheter body 12. An electrode actuator 62 is operably connected to hollow shaft 40 proximate proximal end 64 of hollow shaft 40 to control the extension and retraction of electrode 18 by movement of proximal end 64 of hollow shaft 40. In a preferred embodiment, a stiffening member 66 is provided coaxial with proximal end 64 of the hollow shaft 40 to increase the rigidity of proximal end 64 and prevent bending or crimping thereof during manipulation. An electrode lock mechanism 68 is operably connected to proximal end 64 of hollow shaft 40 to effectively lock electrode 18 in a selected extended or retracted position. In the embodiment shown, electrode lock mechanism is a screw mechanism, although a variety of other frictional and/or mechanical locking mechanisms could be utilized. A tension adjustment mechanism 70 is operably connected to flex tip actuator 60 to adjust a degree of freedom of movement of flex tip actuator 60, and thereby control the feel of the catheter system.

Figure 3:
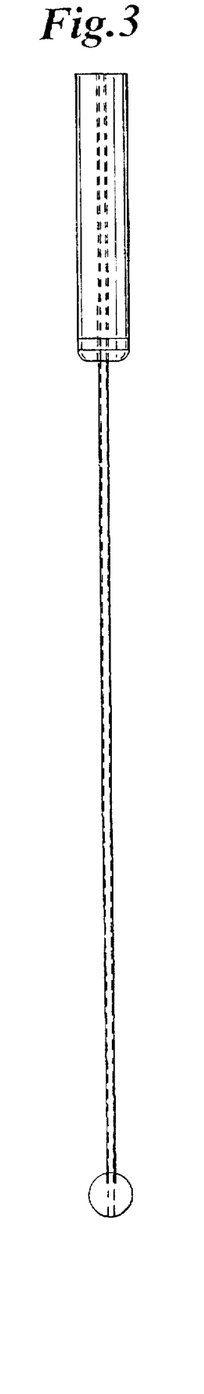
FIG. 3 is detailed schematic representation of a preferred embodiment of the distal end of the present invention.

Referring to FIG. 3, a radiopaque sphere 72 is preferably positioned at a distal end 74 of electrode 18 to aid in positioning electrode 18 under flouroscopy and to prevent distal end 74 of electrode 18 from penetrating tissue. A seal 90 is preferably provided at distal end 16 of catheter body 12 so as to prevent influx of bodily fluids into lumen 28 of catheter body 12. While seal 90 is preferably formed of as a friction fit or heat-shrink seal of distal end 16 of catheter body 12 around electrode 18, any number of various sealing techniques known in the catheter art may be used to create seal 90. As shown in FIG. 5, electrode 18 is also preferably provided with a heat sensor 76 operably coupled to a longitudinal side 30 of electrode 18 to allow an operator to monitor a temperature of electrode 18. As shown in FIG. 1, one or more mapping/stimulation electrodes 78 may be provided on distal end 14 of catheter body 12 to aid in identification of an ablation site or verification of an ablation procedure or to deliver an electrical stimulation pulse. It will be apparent that mapping/stimulation electrodes 78 are best utilized when electrode 18 is carried by catheter body in a retracted position.

In an alternate embodiment as shown in FIG. 6, a strength nandril or guide member 80 within an interior channel 82 of electrode 18 is provided. Guide member 80 provides additional structural integrity to electrode 18 during extension and positioning of electrode 18 and may extended beyond distal end 74 of electrode 18. This added structural integrity aids in preventing a crimping or collapse of interior channel 82 as electrode 18 assumes a desired arcuate shape. Guide member 80 may also be curved to the desired arcuate shape and insert into interior channel 82 of electrode 18 so as to aid in the positioning of electrode 18. Preferably, guide member 80 is selectively withdrawn prior to flushing coolant through electrode 18.

Figure 2:
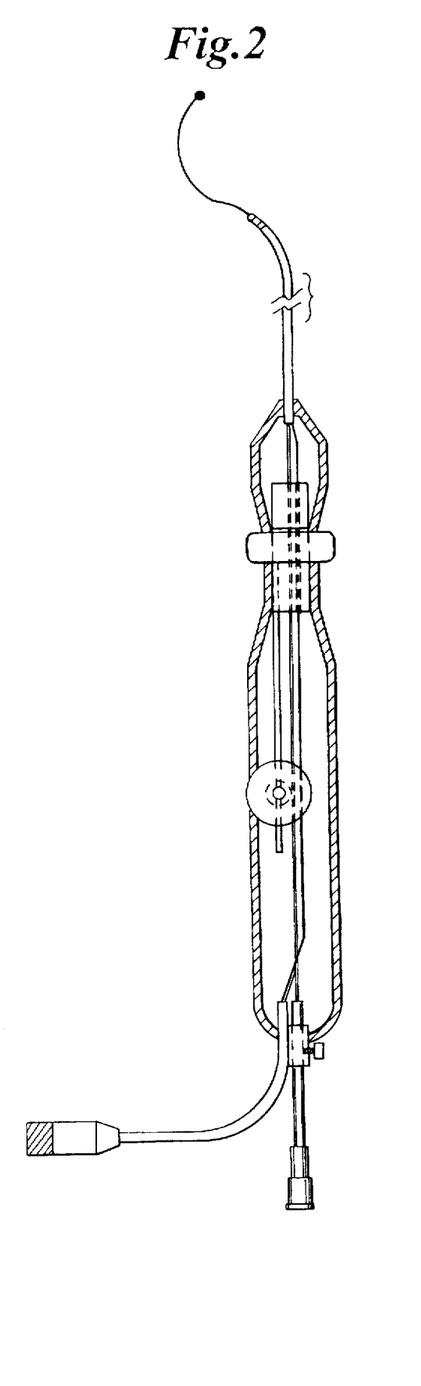
FIG. 2 is a schematic representation as shown in FIG. 1 with the flexible electrode shown in an extended position and forming an arcuate curve.

Referring now to FIG. 2, an alternate embodiment of the RF catheter ablation system of the present invention will be described. In this embodiment, electrode 18 is constructed of a heat shape memory metal such as Nintonal® that is pre-formed at a given activation temperature to a desired arcuate shape and returned to a straight, flexible shape prior to the ablation procedure. During the ablation procedure, electrode 18 will assume the desired shape upon heating electrode 18 with the RF energy to the activation temperature. Electrode 18 is returned to the straight, flexible shape after the linear lesion is created and the temperature of electrode 18 drops below the activation temperature. It will be apparent that such a heat shape memory electrode can assume a wide variety of arcuate formations, depending primarily upon the memory capabilities and tensile strength of the particular heat shape memory material.

Figures 4, 5A:
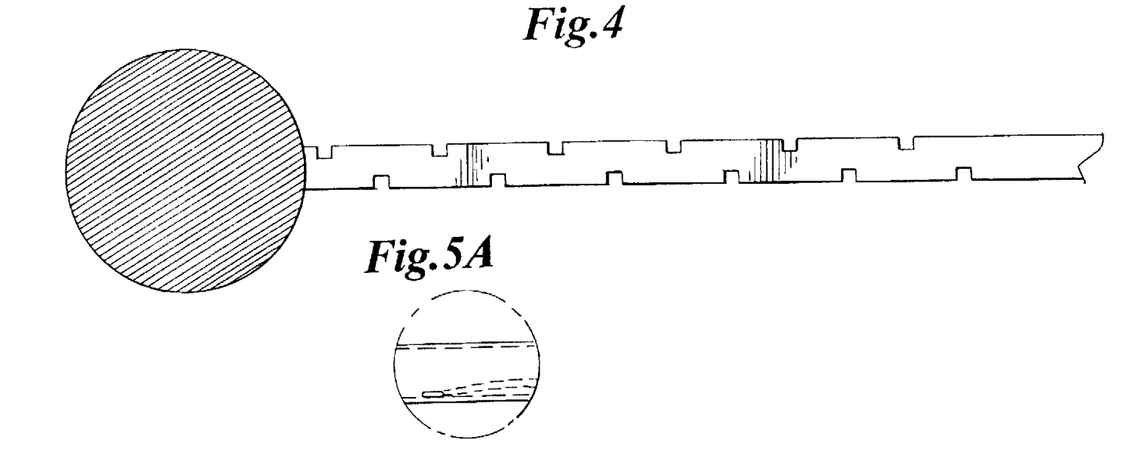
FIG. 4 is detailed schematic representation of an alternate embodiment of the distal end of the present invention showing micro-slotting of the electrode.

In another alternate embodiment as shown in FIG. 4, electrode 18 includes a plurality of micro-apertures 84 defined therein so as to allow for dispersion of the cooling fluid at locations other than distal end 74 of electrode 18. Examples of various kinds of micro-apertures which could be utilized with the present invention are discussed in U.S. Pat. No. 5,462,521, the disclosure of which is hereby incorporated by reference. In one such embodiment, distal end 74 of electrode 18 is plugged to force dispersion of the cooling fluid at locations other than distal end 74. Micro-apertures 84 may also be defined to serve as a plurality of micro-slots defined on alternating longitudinal sides 30 of electrode 18 so as to increase the flexibility of electrode 18.

Referring to FIGS. 7 and 8, in the multiple electrode embodiment of the present invention, two or more electrodes 18-1 and 18-2 may be configured in a spaced-apart, planar relationship (FIG. 7) or three or more electrodes 18-1, 18-2 and 18-3 may be configured in a spaced-apart, three-dimensional relationship, such as a spherical, basket-like arrangement (FIG. 8). In both cases, isolation sleeves 92 are preferably used to insure electrical separation of electrodes 18-1, 18-2 and 18-3 at any points at which the electrodes are adjacent or only closely spaced-apart. In each case, either distal end 74 of electrode 18 or proximal end 94 of electrode 18 may be provided with a containment collar 96 which allows the respective distal end 74 and/or proximal end 94 of electrodes 18-1, 18-2 and 18-3 to slide relative to one another as electrode 18 is deployed. As shown in FIG. 8, distal end 74 may also be provided with a relatively soft tip 96 through which coolant is flushed.

One advantage of the inclusion of cooling and temperature monitoring features in the catheter system 10 is that the temperature of electrode 18 can be controlled so as to remain with a desired range of temperatures by controlling delivery of the RF energy and the cooling fluid of electrode 18. For RF catheter ablation, electrode temperatures are preferably kept within a range of 30° C.–90° C., and optimally within a range of 50° C.–85° C. so as to prevent undesirable coagulation of blood at the ablation site. Due to the very small diameter of the fluid channel within electrode 18, it is also possible to effectively control the temperature of electrode 18 within these desired ranges using a minimum of coolant fluid. Preferably, cooling fluid is provided such that a rate of flow of the cooling fluid through electrode 18 does not exceed 2 ml/minute, and optimally is less than 1 ml/minute. These very low flow rates allow the present invention to make use of conventional cooling supply, such as infusion pumps, instead of requiring specialized cooling supplies.

FIGS. 9–12 show electrode 18 or electrodes 18-1, 18-2 and 18-3 extended and positioned a various ablation sites and in various arcuate shapes. It will be apparent that catheter ablation system 10 may be positioned at a variety of locations within the heart of surrounding vascular system to create the desired linear lesions. In addition to treatment of atrial flutter and atrial fibrillation using the Maze and Corridor procedure, linear lesions created using catheter ablation system 10 may also be used to treat SVT or other atrial arrhythmias. In the case of ventricular arrhythmias, catheter ablation system 10 may be effective in creating linear lesions in the much thicker walls of the ventricle with the application of higher power RF energy and with larger electrodes 18. Additionally, it is possible to use a loop or circular-shaped electrode 18 to create a linear perimeter lesion at a given localized ablation site in the ventricles.

We claim:

1. A radio frequency (RF) linear ablation catheter system comprising:

a flexible, elongated catheter body having a distal end and a proximal end, the catheter body being comprised of a nonconductive, biocompatible material having at least one lumen therethrough;

a flexible, tubular electrode selectively extendable from the distal end of the catheter body, the electrode having structure at a distal end to deter the distal end from penetrating tissue and the electrode flexing into an arcuate linear orientation when extended from the catheter body with the distal end of the electrode and the distal end of the catheter body positioned against a curved interior cardiac wall of a human body such that a portion of a longitudinal side of the electrode exerts a lateral force against the curved interior wall; and means for operating the catheter system, including:

means for remotely manipulating and extending the electrode;

means for providing a cooling fluid which passes through the electrode; and means for providing an RF energy to the electrode for operating in a unipolar mode, such that the electrode simultaneously creates a continuous linear lesion corresponding to the portion of the longitudinal side of the electrode that is positioned against the curved interior cardiac wall of the human body when the electrode is energized.

2. The catheter ablation system of claim 1 wherein the tubular electrode is comprised of a flexible metal needle having an outer diameter ranging from 0.05 mm–0.5 mm and having a tensile strength ranging from 50,000–500,000 psi.

3. The catheter ablation system of claim 1 wherein the tubular electrode has an electrode length of up to 5 cm and has a flexibility that allows arcuate curves to be created which have a chord depth of up to 20 mm.

4. The catheter ablation system of claim 1 wherein the structure at the distal end of the electrode comprises a radiopaque sphere positioned at the distal end of the electrode to aid in positioning the electrode under flouroscopy.

5. The catheter ablation system of claim 1 wherein the electrode includes a plurality of micro-apertures defined therein so as to allow for dispersion of the cooling fluid at locations other than a distal end of the electrode.

6. The catheter ablation system of claim 5 wherein the distal end of the electrode is plugged to force dispersion of the cooling fluid at locations other than the distal end of the electrode.

7. The catheter ablation system of claim 1 wherein the electrode include a plurality of micro-slots defined therein on alternating longitudinal sides of the electrodes so as to increase the flexibility of the electrodes.

8. The catheter ablation system of claim 1 wherein the electrode is constructed of a heat shape memory metal that is pre-formed at a given activation temperature to a desired arcuate shape and returned to a straight, flexible shape prior to the ablation procedure to allow for positioning of the electrode, and that will assume the desired shape upon heating the electrode with the RF energy to the activation temperature and will return to the straight, flexible shape after the linear lesion is created and the temperature of the electrode drops below the activation temperature.

9. The catheter ablation system of claim 1 further comprising a heat sensor operably coupled to the electrode to allow an operator to monitor a temperature of the electrode.

10. The catheter ablation system of claim 1 further comprising a guide member within an interior channel of the electrode that may be selectively withdrawn prior to flushing coolant through the electrode whereby the guide member provides additional structural integrity to the electrode during extension and positioning of the electrode.

11. The catheter ablation system of claim 1 wherein the tubular electrode is comprised of multiple continuous, flexible tubular electrodes such that multiple linear lesion patterns can be created in a single use of the catheter ablation system and wherein a configuration of the multiple electrodes is selected form a set consisting of: at least two flexible, tubular electrodes positioned in a spaced-apart, side-by-side planar arrangement, at least three flexible, tubular electrodes positioned in a spaced-apart, side-by-side planar arrangement, or at least three flexible, tubular electrodes positioned in a spaced-apart, side-by-side three-dimensional spherical arrangement.

12. The catheter ablation system of claim 11 wherein each of the multiple electrodes are operably connected to the means for providing the cooling fluid such that the arrangement of the connection is selected form the set consisting of: independent connection of each electrode to the means for providing the cooling fluid or common connection of all electrodes to the means for providing the cooling fluid, and wherein each of the multiple electrodes are operably connected to the means for providing the RF energy such that the arrangement of the connection is selected from the set consisting of: independent connection of each electrode to the means for providing the RF energy or common connection of all electrodes to the means for providing the RF energy.

13. The catheter ablation system of claim 1 wherein the catheter body includes a catheter shaft and a steerable distal tip section, and wherein the means for operating the catheter system further comprises means for remotely manipulating the steerable distal tip section.

14. The catheter ablation system of claim 13 wherein the means for providing the cooling fluid and the means for providing the RF energy comprise a flexible, conductive hollow shaft disposed with a lumen of the catheter body and having a distal end operably connected to the electrode and a proximal end operably connected to a cooling fluid source and to an RF energy source.

15. The catheter ablation system of claim 14 wherein the hollow shaft and the electrode are formed as an integral piece of conductive tubing having a configuration selected from the set consisting of: a continuous tube having a constant diameter, a continuous tube having a continually tapered diameter, a continuous tube having at least a portion of which has a tapered diameter, a series of tubes of varying degrees of flexibility which are fixed connected together in a coaxial, end-to-end manner, a series of tubes of varying diameters which are fixed connected together in a coaxial, end-to-end manner, or any combination thereof.

16. The catheter ablation system of claim 14 wherein the means for remotely manipulating and extending the electrode and the means for remotely manipulating the distal tip section comprise:
a handle operably connected to the proximal end of the catheter body, the handle including:
a flex tip actuator operably connected to the catheter body proximate a proximal end of the catheter body to control deflection of the distal end of the catheter body;
an electrode actuator operably connected to the hollow shaft proximate a proximal end of the hollow shaft to control the extension and retraction of the electrode by movement of the proximal end of the hollow shaft;
an electrode lock operably connected to the handle and to the hollow shaft proximate the proximal end of the hollow shaft to lock the electrode in a selected extended or retracted position;
a tension adjustment operably connected to the flex tip actuator to adjust a degree of freedom of movement of the flex tip actuator;
an electrical interface operably connected to the proximal end of the hollow shaft and adapted to connect to an external source of RF energy; and
a fluid interface operably connected to the proximal end of the hollow shaft and adapted to connect to an external source of cooling fluid.

17. The catheter ablation system of claim 16 further comprising a stiffening member coaxial with the proximal end of the hollow shaft.

18. The catheter ablation system of claim 1 further comprising at least one mapping/stimulation electrode positioned at the distal end of the catheter body.

19. A method of operating a catheter ablation system to create linear lesions comprising the steps of:
a) providing a catheter ablation system comprised of a flexible, elongated catheter body having a distal end, the catheter body being comprised of a nonconductive, biocompatible material having at least one lumen therethrough, and at least one flexible, tubular electrode selectively extendable form the distal end of the catheter body;

b) introducing the catheter ablation system into a human body and directing the catheter ablation system to a desired location by remotely manipulating the distal end;

c) at the desired location, extending the electrode from the distal end and arcuately positioning at least a portion of a longitudinal side of the electrode against a curved cardiac interior wall of the human body; and d) simultaneously creating at least one continuous linear lesion on the interior cardiac wall of the human body by providing an RF energy to the electrode in a unipolar mode and passing a cooling fluid through the electrode.

20. The method of claim 19 wherein at least one electrode is constructed of a heat shape memory metal that is preformed at a given activation temperature to a desired arcuate shape and returned to a straight, flexible shape prior to the ablation procedure to allow the electrode to be positioned in step c), and wherein steps c) and d) include the steps of heating the electrode with the RF energy to the activation temperature such that the electrode assumes the desired shape, and cooling the electrode with the cooling fluid such that the electrode return to the straight, flexible shape after the linear lesion has been created.

21. The method of claim 19 wherein step d) further comprises the steps of:

d1) monitoring a temperature of the electrode; and d2) adjusting the temperature of the electrode to remain with a desired range of temperatures by controlling delivery of the RF energy and the cooling fluid to the electrode.

22. The method of claim 19 wherein step d) includes the step of dispersing the cooling fluid at locations other than a distal end of the electrode.

23. The method of claim 19 wherein step d) is performed such that a rate of flow of the cooling fluid through the electrode does not exceed 2 ml/minute.

24. The method of claim 19 wherein the distal end of the catheter body is steerable and wherein step c) includes the step of driving the longitudinal side of the electrode into tissue of the interior wall by exerting a force on the electrode using the steerable distal end of the catheter body.

25. A radio frequency (RF) linear ablation catheter system comprising:

a flexible, elongated catheter body having a distal end and a proximal end, the catheter body being comprised of a nonconductive, biocompatible material having at least one lumen therethrough, the catheter body including a catheter shaft and a steerable distal section;

a flexible, tubular electrode having a distal end and a proximal end, the electrode being positioned in a lumen of the catheter body;

a handle operably connected to the proximal end of the catheter body, the handle including:

a flex tip actuator operably connected to the catheter body proximate the proximal end of the catheter shaft to control deflection of the steerable distal section of the catheter body;

an electrode actuator operably connected to the tubular electrode proximate the proximal end of the tubular electrode to control extension and retraction of the electrode relative to the distal end of the catheter body by movement of the proximal end of the tubular electrode;

an electrode lock operably connected to the handle and to the tubular electrode proximate the proximal end of the tubular electrode to lock the electrode in a selected extended or retracted position;

a tension adjustment operably connected to the flex tip actuator to adjust a degree of freedom of movement of the flex tip actuator;

an electrical interface operably connected to the tubular electrode proximate the proximal end of the tubular electrode and adapted to connect to an external source of RF energy for energizing the electrode; and a fluid interface operably connected to the proximal end of the tubular electrode and adapted to connect to an external source of cooling fluid, the flex tip actuator and the electrode actuator being operable such that an extended position of the electrode flexes into an arcuate orientation in an extended position with the distal end of the electrode and the distal end of the catheter body positioned against a curved interior cardiac wall of a human body such that a portion of a longitudinal side of the extended portion of the electrode exerts a lateral force against the curved interior cardiac wall and simultaneously creates a continuous linear lesion when the electrode is energized.

26. The catheter ablation system of claim 25 wherein the extended portion of the tubular electrode has a length of between 0.5 cm–10 cm and has a flexibility that allows arcuate curves to be created which have a chord depth of up to 20 mm.

27. The catheter ablation system of claim 25 further comprising structure proximate the distal end of the electrode to deter the distal end of the electrode from penetrating tissue.

28. The catheter ablation system of claim 25 wherein at least a portion of the extended portion of the tubular electrode includes a plurality of micro-apertures therein so as to allow for dispersion of cooling fluid at locations other than a distal end of the electrode.

29. The catheter ablation system of claim 25 wherein the extended portion of the electrode includes a plural ity of micro-slots defined therein on alternating longitudinal sides of the electrode so as to increase the flexibility of the extended portion of the electrode.

30. The catheter ablation system of claim 25 further comprising a guide member within a lumen of the tubular electrode that may be selectively withdrawn prior to flushing cooling fluid through the tubular electrode whereby the guide member provides additional structural integrity to the electrode during extension and aids the positioning of the electrode once extended from the distal end of the catheter body.

31. The catheter ablation system of claim 25 further comprising at least one mapping/stimulation electrode positioned proximate the distal end of the catheter body.

32. A radio frequency (RF) linear ablation catheter system comprising:

a flexible, elongated catheter body having a distal end and a proximal end, the catheter body being comprised of a nonconductive, biocompatible material having at least one lumen therethrough, the catheter body including a catheter shaft and a steerable distal section;

a flexible, tubular electrode having a distal end and proximal end, the electrode being positioned in the lumen of the catheter body and having an extendable portion of which is selectively extendable from the distal end of the catheter body, the extendable portion including a plurality of micro-slots defined therein on alternating longitudinal sides of the electrode so as to increase the flexibility of the extended portion of the electrode; and means for operating the catheter system, including:

means for remotely manipulating and extending the electrode; and means for providing an RF energy to the electrode.

33. A radio frequency (RF) linear ablation catheter system comprising:

a flexible, elongated catheter body having a distal end and a proximal end, the catheter body being comprised of a nonconductive, biocompatible material having at least one lumen therethrough, the catheter body including a catheter shaft and a steerable distal section;

a flexible, tubular electrode having a distal end and a proximal end, the electrode being positioned in the lumen of the catheter body;

a handle operably connected to the proximal end of the catheter body, the handle including:

a flex tip actuator operably connected to the catheter body proximate the proximal end of the catheter shaft to control deflection of the steerable distal section of the catheter body;

a tension adjustment operably connected to the flex tip actuator to adjust a degree of freedom of movement of the flex tip actuator;

an electrode actuator operably connected to the tubular electrode proximate the proximal end of the tubular electrode to control extension and retraction of the electrode relative to the distal end of the catheter body;

an electrical interface operably connected to the tubular electrode proximate the proximal end of the tubular electrode and adapted to connect to an external source of RF energy; and a fluid interface operably connected to the proximal end of the tubular electrode and adapted to connect to an external source of cooling fluid; and a guide member within a lumen of the tubular electrode that may be selectively withdrawn prior to flushing cooling fluid through the tubular electrode whereby the guide member provides additional structural integrity to the electrode during extension and aids the positioning of the electrode once extended from the distal end of the catheter body.

* * * * *